(12) United States Patent  
Greenberg

(10) Patent No.: US 8,296,952 B2  
(45) Date of Patent: Oct. 30, 2012

(54) ORTHODONTIC TREATMENT ALIGNERS BASED ON CT DATA

(75) Inventor: Alex M. Greenberg, New York, NY (US)

(73) Assignee: Greenberg Surgical Technologies, LLC, New York, NY (US)

( * ) Notice: Subject to any disclaimer, the term of this patent is extended or adjusted under 35 U.S.C. 154(b) by 1031 days.

(21) Appl. No.: 12/290,745

(22) Filed: Nov. 3, 2008

(65) Prior Publication Data

US 2009/0113714 A1    May 7, 2009

Related U.S. Application Data

(60) Provisional application No. 61/001,341, filed on Nov. 1, 2007.

(51) Int. Cl.
*B21F 43/00* (2006.01)
(52) U.S. Cl. ............................. 29/896.11; 433/3; 433/24
(58) Field of Classification Search ............... 29/896.11; 433/3, 24
See application file for complete search history.

(56) References Cited

U.S. PATENT DOCUMENTS

| | | | |
|---|---|---|---|
| 5,139,419 A | 8/1992 | Andreiko et al. | |
| 7,056,115 B2 * | 6/2006 | Phan et al. | 433/24 |
| 7,387,511 B2 * | 6/2008 | Marshall | 433/3 |
| 7,474,307 B2 * | 1/2009 | Chishti et al. | 345/418 |
| 7,837,464 B2 * | 11/2010 | Marshall | 433/3 |
| 2005/0084144 A1 | 4/2005 | Feldman | |

* cited by examiner

*Primary Examiner* — Richard Chang
(74) *Attorney, Agent, or Firm* — Cozen O'Connor

(57) ABSTRACT

A system and method for orthodontic alignment includes a radiographic template. The radiographic template has a plurality of metallic markers. A negative impression of a patient's dental arch is made. At least one orthodontic treatment aligner is produced. The aligner is manufactured based in part on a computed axial tomography (CT) scan of a patient wearing the radiographic template and a separate scan of the radiographic template, wherein the data is processed by superimposition of the orthodontic aligner on the CT images of the patient including a jaw in axial and panoramic views. In this manner, the tooth above the gum line, represented by the negative impression as well as the tooth below the gum line, represented by the CT data is used to design the orthodontic aligner.

10 Claims, 5 Drawing Sheets

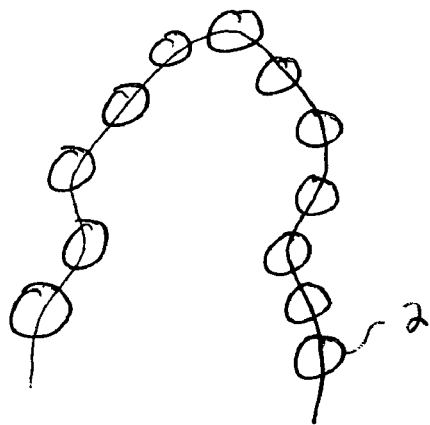
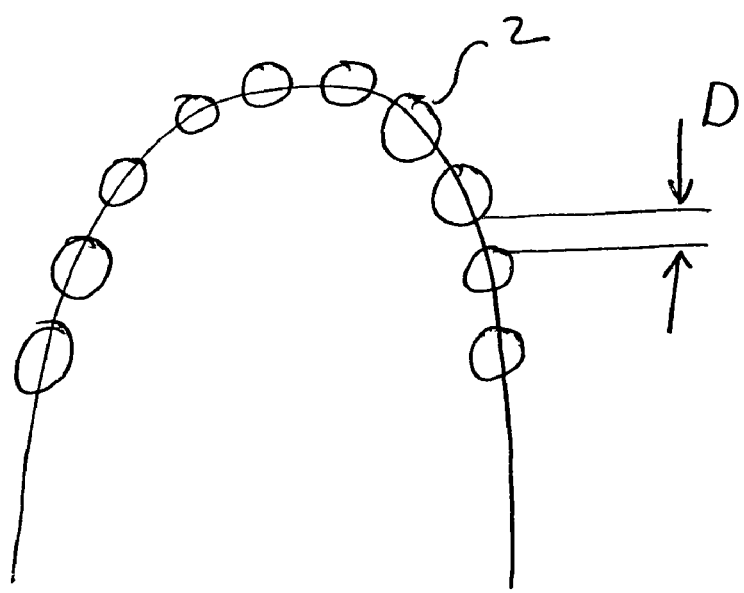
PRIOR ART

ORTHODONTIC TREATMENT ALIGNERS BASED ON CT DATA

RELATED APPLICATIONS

This application claims priority from U.S. Provisional Patent Application Ser. No. 61/001,341, which was filed on Nov. 1, 2007, the entirety of which is herein incorporated by reference.

BACKGROUND OF THE INVENTION

1. Field of the Invention

This invention relates generally to the field of orthodontic appliances. More specifically, the present invention relates to a process for designing and manufacturing orthodontic aligners for use in orthodontic treatment in which individual teeth are urged along predetermined paths so as to cause realignment thereof.

2. Description of the Related Art

Dentistry is currently involved in a process of rapid change in what has until recently been considered conventional practice. Such changes are taking place in many fields and are often the result of the integration of new computer-based digital technologies, which tend to become the core of powerful new methodologies. In the dental specialty of orthodontics, for example, the process of laser scanning and three-dimensional imaging of a patient's teeth and then the manipulation of the virtual tooth positions within a computer-aided-design (CAD) environment utilize these new technologies. Orthodontists and some dentists routinely use three-dimensional imaging and CAD manipulation of tooth positions and tooth relationships as part of an approach to straightening teeth.

To use the digital services, an impression of a patient's teeth, gums, and soft tissue is taken. From the impression, a positive stone model is poured and allowed to cure. Instead of retaining a patient's models for in-office case diagnosis and treatment planning as in the past, the attending orthodontist will instead ship the patient's models to a regional commercial orthodontic service center. A number of services are available to a doctor using such service centers, and these services will be provided according to a prescription and other instructions sent along with the patient's models to the service center.

U.S. Pat. No. 5,139,419 (Andreiko) discloses a methodology beginning with scanning of a patient's models as described above to produce a digital code that can be assimilated by computer software. For this step, models can be scanned by any of several current methods to create digital code representing a virtual model of the teeth above the gum line, gums, and soft tissues that can be visually displayed on a computer screen. Andreiko describe methods for the virtual separation of individual teeth from adjacent teeth and soft tissues, and methods for bodily repositioning of individual teeth and groups of teeth.

FIG. 1 is an occlusal view of a dental malocclusion. As shown, teeth 2 are not properly aligned. The dental malocclusions shown in FIG. 1 are typically corrected with a series of orthodontic aligners. The orthodontic aligners are typically manufactured based on dental casts that are optically scanned as discussed above. One or more orthodontic aligners are user during the treatment to realign the teeth.

FIG. 2 depicts a set of teeth that have undergone treatment using the optically scanned dental casts. The aligned teeth have a spacing D. This space between the teeth is based in part on using data regarding the teeth above the gum line, without considering the roots of the teeth.

SUMMARY OF THE INVENTION

A system for orthodontic alignment includes a radiographic template. The radiographic template has a plurality of metallic markers. A negative impression of a patient's dental arch is made. At least one orthodontic treatment aligner is produced. The aligner is manufactured based in part on a computed axial tomography (CT) scan of a patient wearing the radiographic template and a separate scan of the radiographic template, wherein the data is processed by superimposition of the orthodontic aligner on the CT images of the patient including a jaw in axial and panoramic views. In this manner, the tooth above the gum line, represented by the negative impression as well as the tooth below the gum line, represented by the CT data is used to design the orthodontic aligner.

A method of manufacturing a template for orthodontic movement of at least one tooth includes several steps. A malleable material and a plurality of radio-opaque markers are placed in contact with a tooth surface. A negative impression of the tooth surface is formed by conforming the malleable material to at least a portion of the tooth surface. Radio-opaque markers are located at defined positions in the material in contact with the tooth surface. Two radiographs, CT scans are taken, a first radiograph of the tooth surface and the malleable material and a second radiograph of the negative impression apart from the tooth surface. The first and second radiographs are compared to determine the entire shape of the tooth surface, including the root. A desired location for the at least one tooth is then determined. A desired position for the at least one tooth at the desired location is then determined. A desired movement of for the at least one tooth at the desired location is then determined. An aligner for orthodontic movement for the at least one tooth is then formed. The orthodontic aligner conforms to the negative impression and includes an altered form of the negative impression along the desired position for the at least one tooth so that the aligner contacts the tooth surface to effect orthodontic movement of the at least one tooth at the desired location.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

The invention will be explained in more detail with reference to the drawing, which illustrates only exemplary embodiments. In the drawing:

FIG. 1 is an occlusal view of a dental malocclusion;

FIG. 2 is an occlusal view after orthodontic treatment;

DETAILED DESCRIPTION OF THE PRESENTLY PREFERRED EMBODIMENTS

A patient seeking to correct a dental malocclusion visits an orthodontist. FIG. 1 depicts the dental occlusion. To treat the dental malocclusion, the orthodontist makes an orthodontic appliance that is a negative impression of the dental arch. The orthodontic appliance is made with a malleable material. The orthodontic appliance is preferably formed of acrylic, silicone, or other suitable radio-transparent material. The material preferably completely conforms to the entirety of each tooth crown of the negative impression. The orthodontic aligner can be placed and removed. In a preferred embodiment, at least 6 fiducial markers are placed on the appliance at the buccal or lingual surfaces of the teeth at a known distance from the crowns, because the crowns typically contain metallic restorations. The fiducial markers are wires or other radio-opaque markers placed to outline the buccal, incisal, and lingual contours. Preferably, one or more teeth are marked. In a preferred embodiment, the radio opaque markers are of titanium to avoid scatter interference.

Figure 3:
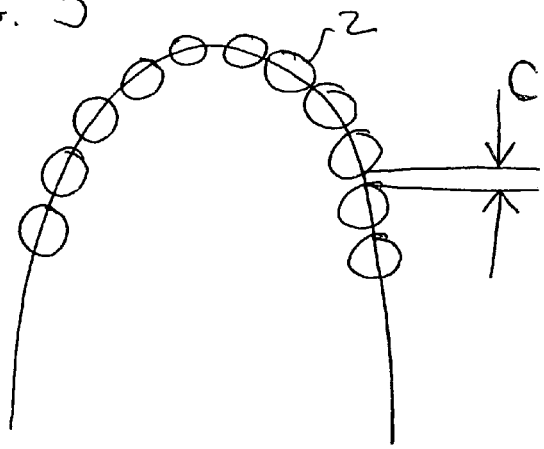
FIG. 3 is an occlusal view after orthodontic treatment in accordance with an embodiment of the invention.

The patient wears the appliance during a CT scan. After the scan, the appliance is scanned separately, i.e. without it being worn by the patient, but preferably in the same orientation as when the patient was wearing it. The CT scans are used to generate a three-dimensional image each tooth from a large series of two-dimensional X-ray images preferably taken around a single axis of rotation. The data from both scans is then uploaded and processed by medical image processing algorithms. Preferably, the data is in a Digital Imaging and Communications in Medicine (dicom) format. In this manner, complete data for each tooth, both above and below the gum line is obtained. It should be further noted that due to the CT scans, no mold of the teeth above the gum line is required. Registration of the fiducial markers is performed and the two data sets are superimposed. The two data sets are merged using a computer program such as the one disclosed in the referenced published U.S. Patent Application No. 2005/0084144 using the radiographic markers as the points of alignment. The data is then processed with superimposition of the orthodontic aligner on the CT images of the jaw in axial and panoramic views. A series of orthodontic aligners are produced based on the CT data. It should be noted that no mold has to be produced due to the data in the CT images. After treatment with the series of orthodontic aligners, the patient's teeth are aligned as shown in FIG. 3. As shown, the teeth have a spacing C, which is smaller than the spacing D in the prior art.

Figure 4A:
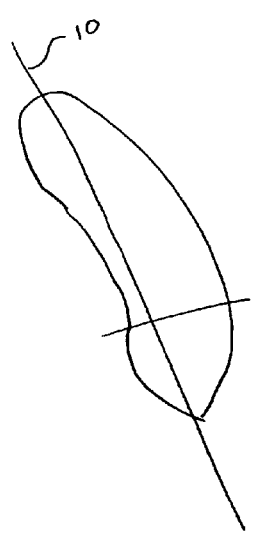
FIG. 4a is depiction of an incisor.
Figure 4B:
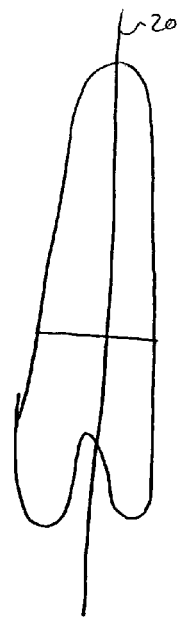
FIG. 4b is a depiction of a premolar.
Figure 4C:
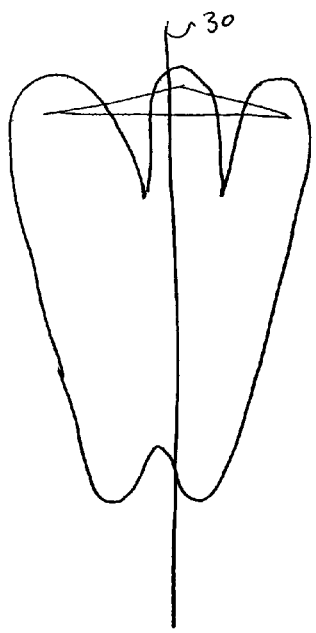
FIG. 4c is a depiction of a molar.

As shown in FIG. 4*a*, software tools are used to place an alignment line 10 bisecting the apex of the tooth through the incisal edge of incisors. Similarly, FIG. 4*b* shows an alignment line 20 drawn at the central fossa of a premolar and FIG. 4*c* shows an alignment line 30 drawn at the central fossa of a molar. For multiple rooted teeth, such as a molar, an average of the root apices is created and the bisecting line is oriented through the central fossa of the tooth. In a preferred embodiment, a computer program is used in which there is a representation of these alignment lines in a panoramic view, depicting the tooth coronal-apical trajectories.

Figure 5:
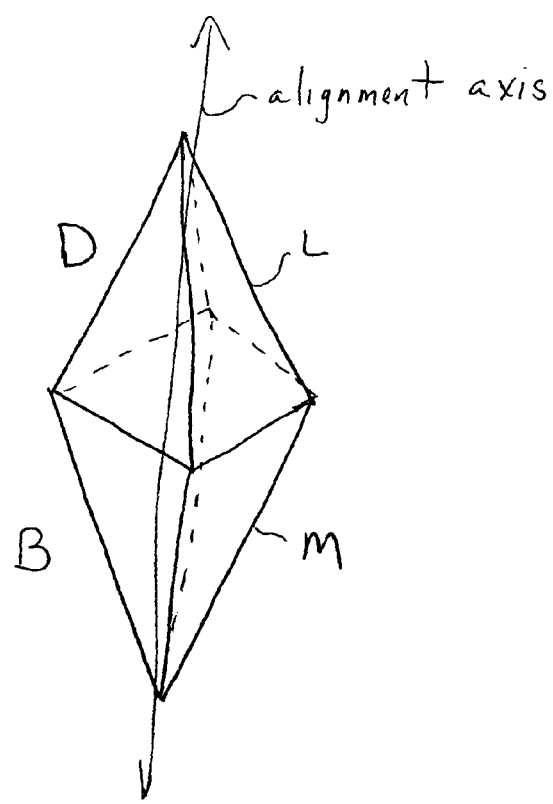
FIG. 5 is 3D representation of a tooth.

Each individual tooth can be manipulated into a desired position, which correlates to a 3D image of the dentition. As shown in FIG. 5, each tooth is represented by a 3D image, which is a pair of tetrahedrons connected at the bases with apices as opposing pyramids. An alignment axis passes through each apex and each side corresponding to one of the buccal, lingual, mesial, and distal aspects of each tooth. Preferably, all of the teeth in undergo automatic conversion to these dual tetrahedrons. In one embodiment, for multi-root teeth, a tetrahedron is added which represents each root.

Figure 6:
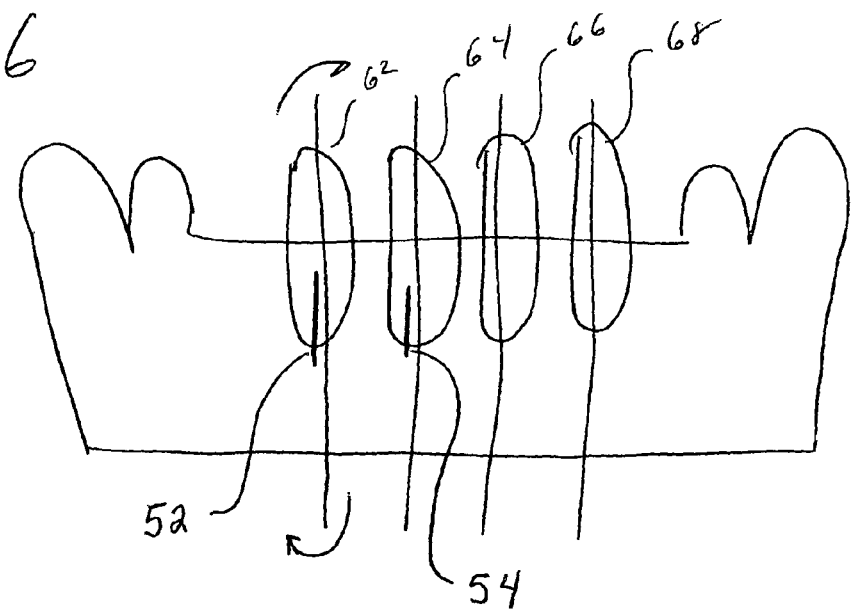
FIG. 6 is a panoramic view of a patients dentition.
Figure 7:
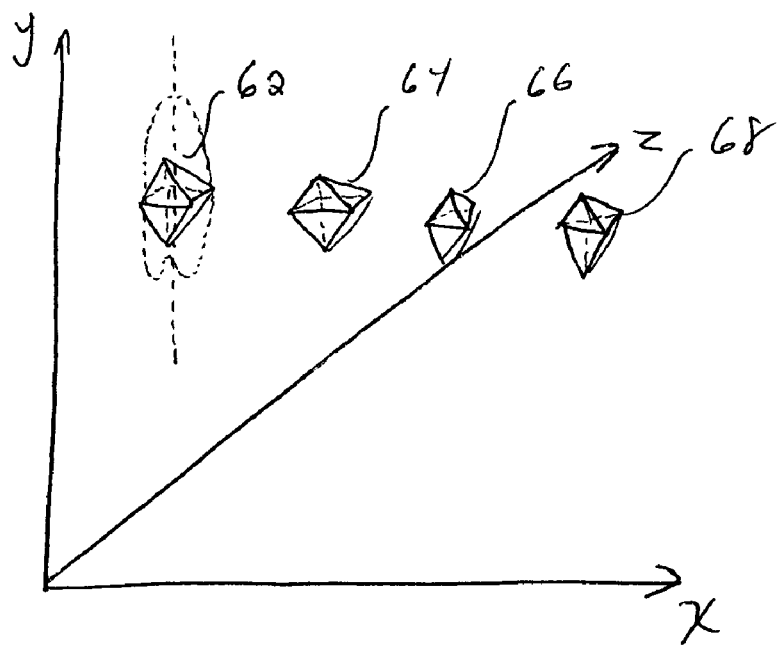
FIG. 7 is a 3D representation of a patients dentition.
Figure 8:
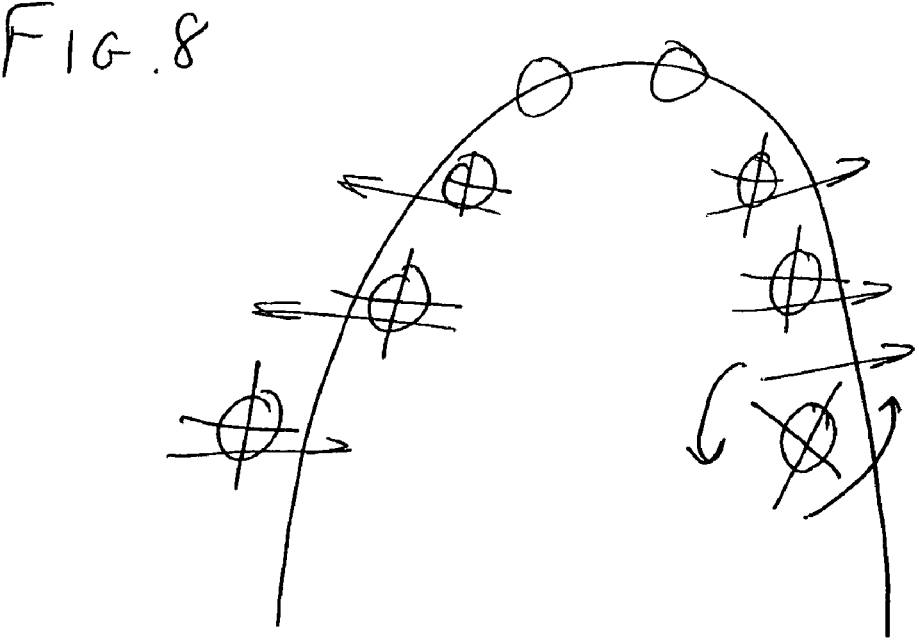
FIG. 8 an orthodontic alignment plan.

A panoramic view is created as shown in FIG. 6. Once the panoramic view is created manipulation of the alignment plane is performed which correlates in real time to the 3D image of the dentition. The panoramic view includes the teeth 62, 64, 66, and 68 as well as additional fiducial markers 52 and 54. A corresponding 3D image is shown in FIG. 7. The 3D image depicts the spatial relationships between the teeth being adjusted. A corresponding sagittal view, shown in FIG. 8, depicts the required manipulation for each tooth. The alignment of each tooth is performed which correlates in real time to a 3D image of the dentition.

The axial views are manipulated in a similar manner with correlation to a 3D image of the dentition. The 3D treatment positioning of the teeth in the final desired outcome of the treatment is displayed as shown in FIG. 7. The orthodontic aligner used to reposition the teeth is registered using the fiducial markers or optically scanned data of the dentition. The paired tetrahedrons, with the ability to further superimpose the shape of the individual teeth and roots based on the CT scan data and a positive impression of the virtual negative impression of the radiographic, are used to design the orthodontic aligner. It should be noted that the original radiographic aligner and the fiducial markers provide a reference baseline from which the teeth are moved either individually or as a group. Additionally, because the CT scan included the roots and jaw, an improved orthodontic aligner is produced.

Using the fiducial markers, the original radiographic aligner is aligned in the 3D space grid. The practitioner approves of the final treatment plan, decides on an appropriate tooth position for each tooth, and allows software to convert the data of the radiographic orthodontic aligner template into a treatment orthodontic aligner. The alignment software typically has appropriate 3D representations of the tooth positions and the movement of each tooth corresponds to a 3D grid. Each tooth is individually mapped in the 3D space and is mapped in relation to the other teeth. The individual teeth can then be further manipulated into the desired position. In other words, a triangulation occurs between the rotation, intrusion, tipping, extrusion, or bodily movement of the teeth and the alignment line.

The serial planned tooth movements in orthodontics require: tipping, bodily movement, rotation, intrusion, and extrusion. This change is then virtually translated in the orthodontic aligner. The final orthodontic treatment aligner with the new tooth positions is approved and a video of the planned movement is reviewed. The virtual orthodontic aligners are sent via e-mail or burned on a CD ROM to the manufacturer for a rapid manufacturing process that results in production of the orthodontic treatment aligner as a series.

As individual or multiple teeth are moved, the software changes the position of each tooth and, by using the alignment lines, ensures that the movement of the tooth avoids contact between tooth roots which is provided by the CT data. Therefore, a triangulation occurs between the rotation, intrusion, tipping, extrusion or bodily movement of the tooth and the alignment line. This change is then virtually translated in the orthodontic aligner, which is a digital conversion of the radiographic aligner, with the new tooth positions from the digitally converted aligner sent to a 3D printer for production. Each video clip of each stage of the orthodontics is accomplished with a different aligner produced by the 3D printer.

Figure 9:
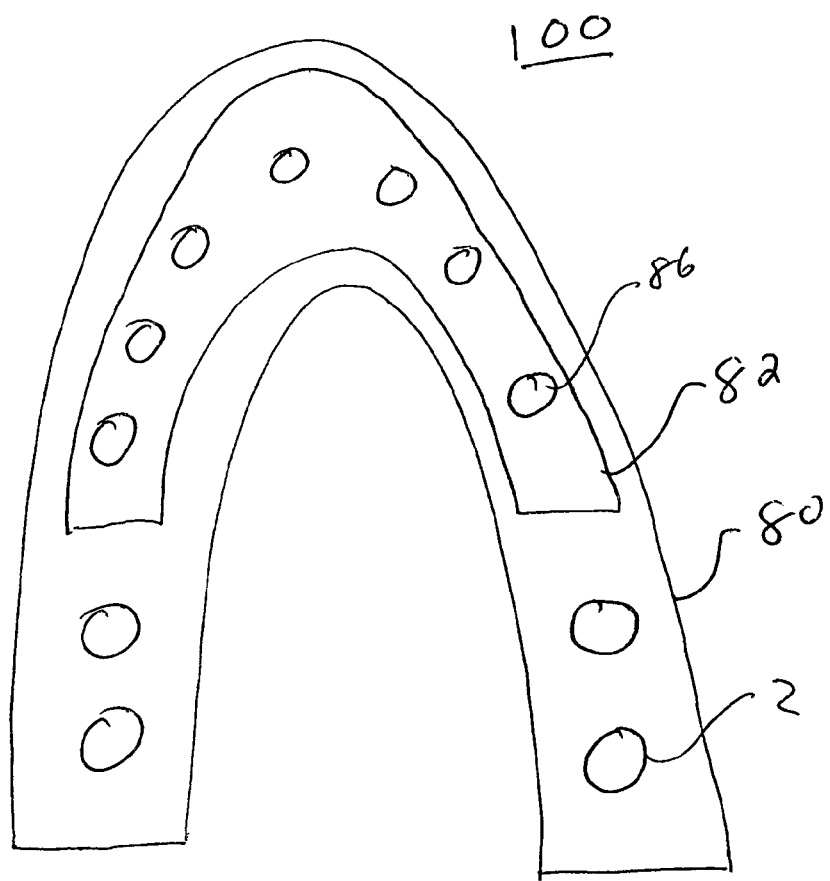
FIG. 9 is an aligner in accordance with one embodiment of the invention.

In one embodiment, as shown in FIG. 9, a modular aligner 100 is created. In one embodiment, only the portion of the aligner 82 that is concerned with the tooth movement is produced. These inserts 82 are easier to manufacture than an entire alignment device. As the realignment of the teeth is effected, the inserts 82 are changed until the overall treatment plan is completed. The original or subsequent orthodontic aligners as inserts reduce the production time, amount of material used, and cost. In another embodiment, the aligner 82 and the frame are a single structure.

Additionally, other features can be incorporated into the aligner 82. In one embodiment, the aligner 82 creates a space for a dental implant. The aligner 82 would then include an element such as a sleeved stop for a drill bit, as disclosed in U.S. Pat. No. 7,210,881 and U.S. application Ser. No. 11/157, 882, the both of which are incorporated herein by reference in their entirety.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps, which perform substantially the same function in substantially the same way to achieve the same results, are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

I claim:

1. A method of manufacturing a template for orthodontic movement of at least one tooth, said method comprising:
    forming a radiographic template, the radiographic template having a plurality of metallic markers and being a negative impression of the at least one tooth;
    taking a first CT scan of said tooth surface and the radiographic template, including at least one tooth root;
    removing the radiographic template from said tooth surface;
    taking a second CT scan of the radiographic template apart from said tooth surface;
    comparing the first and second CT scans to determine the shape of said tooth surface;
    forming an aligner for orthodontic movement for the at least one tooth, the aligner based at least in part on the first CT scan and the at least one tooth root, said aligner conforming to said radiographic template and including an altered form of said radiographic template along said desired position for the at least one tooth so that said aligner contacts said surface to effect orthodontic movement of the at least one tooth at a desired location.

2. The method of manufacturing a template for orthodontic movement of at least one tooth, according to claim 1, wherein the radiographic template is formed by:
    placing a malleable material and a plurality of radio-opaque markers in contact with the tooth surface;
    forming a negative impression of said tooth surface by conforming said malleable material to at least a portion of said tooth surface; and
    locating said radio-opaque markers at defined positions in said material in contact with said tooth surface.

3. The method of manufacturing a template for orthodontic movement of at least one tooth, according to claim 2, the method further comprising:
    determining the desired location for the at least one tooth;
    determining a desired position for the at least one tooth at the desired location; and
    determining a desired movement of for the at least one tooth at said desired location.

4. The method of manufacturing a template for orthodontic movement of at least one tooth, according to claim 1, wherein said final orthodontic position is achieved through a plurality of aligners fabricated from a series of projected tooth positions that achieve the desired orthodontic biomechanical movement.

5. The method of manufacturing a template for orthodontic movement of at least one tooth, according to claim 4, further comprising placing alignment lines bisecting an apex of the tooth through an incisal edge of an incisor and a central fossa of premolar and molar teeth.

6. The method of manufacturing a template for orthodontic movement of at least one tooth, according to claim 4, wherein only the position of the alignment that is involved in tooth movement is produced, which can be changed in the original orthodontic aligner as an insert.

7. The method of manufacturing a template for orthodontic movement of at least one tooth, according to claim 4, wherein a portion of a surgical template contains a guideway that has a portion made of a modular material that can be removed from the radiographic template and scanned.

8. The method of manufacturing a template for orthodontic movement of at least one tooth, according to claim 1, further comprising uploading data from both scans and processing the data by medical image processing algorithms.

9. The method of manufacturing a template for orthodontic movement of at least one tooth, according to claim 8, wherein the data is uploaded in a dicom format.

10. A method of manufacturing a template for orthodontic movement of at least one tooth, the method comprising:
    placing a malleable material and a plurality of radio-opaque markers in contact with a tooth surface;
    forming a negative impression of said tooth surface by conforming said malleable material to at least a portion of said tooth surface;
    locating the radio-opaque markers at defined positions in said malleable material in contact with said tooth surface;
    imaging said tooth surface and said malleable material with radio-opaque markers to create a first image, including a tooth root;
    imaging the malleable material with radio-opaque markers apart from said tooth surface to create a second image;
    comparing the said first and second images to determine the entire shape of said tooth surface, including the root;
    determining a desired location for the at least one tooth;
    determining a desired position for the at least one tooth at the desired location;
    determining a desired movement of for the at least one tooth at said desired location; and
    forming an aligner for orthodontic movement of said for the at least one,
    wherein the aligner conforms to the negative impression and includes an altered form of the negative impression so that the aligner contacts the tooth surface to effect orthodontic movement of the at least one tooth at said desired location.

* * * * *